US00RE40002E

(19) United States
(12) Reissued Patent
Lin

(10) Patent Number: US RE40,002 E
(45) **Date of Reissued Patent: *Jan. 15, 2008**

(54) TREATMENT OF PRESBYOPIA AND OTHER EYE DISORDERS USING A SCANNING LASER SYSTEM

(75) Inventor: Jui-Teng Lin, Coleman, FL (US)

(73) Assignee: SurgiLight, Inc., Orlando, FL (US)

( * ) Notice: This patent is subject to a terminal disclaimer.

(21) Appl. No.: 10/626,486

(22) Filed: Jul. 24, 2003

(Under 37 CFR 1.47)

Related U.S. Patent Documents

Reissue of:
(64) Patent No.: 6,263,879
Issued: Jul. 24, 2001
Appl. No.: 09/189,609
Filed: Nov. 10, 1998

(51) Int. Cl.
*A61B 19/00* (2006.01)

(52) U.S. Cl. ..... 128/898; 606/4; 606/5; 606/10; 606/11; 607/89

(58) Field of Classification Search ..... 128/898; 606/3–5, 10, 11, 17, 107; 607/89
See application file for complete search history.

(56) References Cited

U.S. PATENT DOCUMENTS

| | | | | |
|---|---|---|---|---|
| 4,592,065 | A | 5/1986 | de Witte | |
| 4,755,999 | A | 7/1988 | Macken | |
| 4,773,414 | A | 9/1988 | L'Esperance, Jr. | |
| 4,846,172 | A | 7/1989 | Berlin | |
| 4,907,586 | A * | 3/1990 | Bille et al. | 606/5 |
| 5,019,074 | A | 5/1991 | Muller | |
| 5,102,409 | A | 4/1992 | Balgorod | |
| 5,108,388 | A | 4/1992 | Trokel | |
| 5,144,630 | A | 9/1992 | Lin | |
| 5,152,760 | A | 10/1992 | Latina | |
| 5,163,934 | A | 11/1992 | Munnerlyn | |
| 5,354,331 | A | 10/1994 | Schachar | |
| 5,423,801 | A | 6/1995 | Marshall et al. | |
| 5,465,737 | A | 11/1995 | Schachar | |

(Continued)

FOREIGN PATENT DOCUMENTS

WO WO 98/41177 9/1998

OTHER PUBLICATIONS

Sher, Surgery for Hyperopia and Presbyopia, Oct. 1997, Williams & Wilkens, First Edition, 33–36.*
Thornton, Spencer P., *Anterior Ciliary Sclerotomy (ACS), A Procedure to Reverse Presbyopia,* in "Surgery for Hyperopia and Presbyopia", Oct. 1997, pp. 33–36 (chapter 4), published by Williams & Wilkins.

*Primary Examiner*—Lee S. Cohen
(74) *Attorney, Agent, or Firm*—Knobbe, Martens, Olson & Bear LLP

(57) ABSTRACT

Presbyopia is treated by a method which uses ablative lasers to ablate the sclera tissue and increase the accommodation of the ciliary body. Tissue bleeding is prevented by an ablative laser having a wavelength of between 0.15 and 3.2 micron. A scanning system is proposed to perform various patterns on the sclera area of the cornea to treat presbyopia and to prevent other eye disorder such as glaucoma. Laser parameters are determined for accurate sclera expansion.

REEXAMINATION RESULTS
The questions raised in reexamination request no. 90/006, 090, filed Aug. 22, 2001, have been considered and the results thereof are reflected in this reissue patent which constitutes the reexamination certificate required by 35 U.S.C. 307 as provided in 37 CFR 1.570(e), for ex parte reexaminations, or the reexamination certificate required by 35 U.S.C. 316 as provided in 37 CFR 1.997(e) for inter partes reexaminations.

23 Claims, 3 Drawing Sheets

U.S. PATENT DOCUMENTS 5,484,432 A 1/1996 Sand
5,490,849 A * 2/1996 Smith ..... 606/5
5,520,679 A 5/1996 Lin
5,529,076 A 6/1996 Schachar
5,533,997 A * 7/1996 Ruiz ..... 606/5
5,549,598 A 8/1996 O'Donnell, Jr.
5,599,341 A 2/1997 Mathis et al.
5,630,810 A 5/1997 Machat
5,722,952 A 3/1998 Schachar
5,738,676 A 4/1998 Hammer et al.
5,741,247 A 4/1998 Rizoiu et al.
5,782,822 A 7/1998 Telfair et al.
5,803,923 A 9/1998 Singh-Derewa et al.
5,845,024 A 12/1998 Tsushima et al.
5,891,131 A 4/1999 Rajan et al.
5,928,129 A 7/1999 Ruiz
5,984,916 A 11/1999 Lai
5,997,529 A 12/1999 Tang et al.
6,010,497 A 1/2000 Tang et al.
6,019,754 A 2/2000 Kawesch
6,090,100 A 7/2000 Hohla
6,090,102 A 7/2000 Telfair et al.
6,099,522 A 8/2000 Knopp et al.
6,132,424 A 10/2000 Tang
6,156,030 A 12/2000 Neev
6,161,546 A 12/2000 Yavitz
6,171,336 B1 1/2001 Sawusch
6,190,374 B1 2/2001 Amano et al.
6,197,018 B1 3/2001 O'Donnell, Jr.
6,197,056 B1 3/2001 Schachar
6,203,538 B1 3/2001 Peyman
6,210,401 B1 4/2001 Lai
6,258,082 B1 7/2001 Lin
6,263,879 B1 7/2001 Lin
6,280,435 B1 8/2001 Odrich et al.
6,364,871 B1 4/2002 Sotiropoulos et al.
6,745,775 B2 6/2004 Lin
6,824,540 B1 11/2004 Lin
2001/0029363 A1 10/2001 Lin
2003/0220630 A1 11/2003 Lin et al.

* cited by examiner

TREATMENT OF PRESBYOPIA AND OTHER EYE DISORDERS USING A SCANNING LASER SYSTEM

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates to methods and apparatus for the treatment of presbyopia and the treatment and prevention of glaucoma using dual-beam scanning lasers.

2. Prior Art

Corneal reshaping, including a procedure called photorefractive keratectomy (PRK) and a new procedure called laser assisted in situ keratomileusis, or laser intrastroma keratomileusis (LASIK), has been performed by lasers in the ultraviolet (UV) wavelength of 193–213 nm. Commercial UV refractive lasers include ArF excimer lasers at 193 nm and other non-excimer, solid-state lasers, such as the one patented by the present inventor in 1992 (U.S. Pat. No. 5,144,630). Precise, stable corneal reshaping requires lasers with strong tissue absorption (or minimum penetration depth) such that the thermal damage zone is at a minimum (less than few microns). Furthermore, accuracy of the procedure of vision correction depends on the amount of tissue removed in each laser pulse, in the order of about 0.2 microns. Therefore, lasers at UV wavelengths between 193 and 213 nm and at the mid-infrared wavelengths between 2.8 and 3.2 microns are two attractive wavelength ranges which match the absorption peak of protein and water, respectively.

The above-described prior arts are however limited to the use of reshaping the corneal surface curvature for the correction of myopia and hyperopia. A variation of farsightedness that the existing laser surgery procedures will not treat is presbyopia, and the gradual age related condition of suddenly fuzzy print and the necessity of reading glasses. When a person reaches a certain age (around 40), the eyes start to lose their capability to focus sharply for near vision. Presbyopia is not due to the cornea but comes about as the lens loses its ability to accommodate or focus sharply for near vision as a result of loss of elasticity that is inevitable as people age.

Thermal lasers such as Ho:YAG have been proposed for the correction of hyperopia by laser-induced coagulation of the corneal. The present inventor has also proposed the use of a laser-generated bifocal for the treatment of presbyopic patients but fundamental issues caused by age of presbyopic patients still remains unsolved in those prior approaches.

To treat presbyopic patients, or the reversal of presbyopia, using the concept of expanding the sclera by mechanical devices has been proposed by Schaker in U.S. Pat. Nos. 5,529,076, 5,722,952, 5,465,737 and 5,354,331. These mechanical approaches have the drawbacks of complexity and are time consuming, costly and have potential side effects. To treat presbyopia, the Schaker U.S. Pat. Nos. 5,529,076 and 5,722,952 propose the use of heat or radiation on the corneal epithelium to arrest the growth of the crystalline lens and also propose the use of lasers to ablate portions of the thickness of the sclera. However, these prior arts do not present any details or practical methods or laser parameters for the presbyopic corrections. No clinical studies have been practiced to show the effectiveness of the proposed concepts. The concepts proposed in the Schaker patents regarding lasers suitable for expanding the sclera tissues were incorrect in that the proposed lasers did not identify those which are "cold lasers" and can only conduct the tissue ablation rather than thermal burning of the cornea. Furthermore, the clinical issues, such as accuracy of the sclera tissue removal and potential tissue bleeding during the procedures, were not indicated in these prior patents. In addition, it is essential to use a scanning laser to achieve the desired ablation pattern and to control the ablation depth on the sclera tissue.

One objective of the present invention is to provide an apparatus and method to obviate these drawbacks in the above Schaker patents.

It is yet another objective of the present invention to provide an apparatus and method which provide the well-defined laser parameters for efficient and accurate sclera expansion for presbyopia reversal and the treatment and preventing of open angle glaucoma.

It is yet another objective of the present invention to use a scanning device such that the degree of ciliary muscle accommodation can be controlled by the location, size and shapes of the removed sclera tissue.

It is yet another objective of the present invention to define the non-thermal lasers for efficient tissue ablation and thermal lasers for tissue coagulation. This system is able to perform both in an ablation mode and in a coagulation mode for optimum clinical outcomes. It is yet another objective of the present invention to provide an integrated system in which dual-beam lasers can be scanned over the corneal surface for accurate ablation of the sclera tissue without bleeding, with ablation and coagulation laser beams simultaneously applied on the cornea.

It is yet another objective of the present invention to define the optimal laser parameters and the ablation patterns for best clinical outcome for presbyopia patients, where sclera expansion will increase the accommodation of the ciliary muscle.

It is yet another objective of the present invention to provide the appropriate scanning patterns which will cause effective sclera expansion.

SUMMARY OF THE INVENTION

The preferred embodiments of the present surgical laser consists of a combination of an ablative-type laser and a coagulative-type laser. The ablative-type laser has a wavelength range of from 0.15 to 0.35 microns and from 2.6 to 3.2 microns and is operated in a Q-switch mode such that the thermal damage of the corneal tissue is minimized. The coagulative-type lasers includes a thermal laser having a wavelength of between 0.45 and 0.9 microns and between 1.5 and 3.2 microns, and between 9 and 12 microns operated at a long-pulse or continuous-wave mode.

It is yet another preferred embodiment of the present invention to provide a scanning mechanism to effectively ablate the sclera tissue at a controlled depth by beam overlapping.

It is yet another preferred embodiments of the present invention to provide an apparatus and method such that both the ablative and the coagulative lasers can have applied to their beams the corneal surface to thereby prevent bleeding during the procedure.

It is yet another embodiment of the present invention to provide an integration system in which a coagulative laser may have the beam delivered by a scan or by a fiber-coupled device which can be manually scanned over the cornea. It is yet another embodiment of the present invention to focus the laser beams in a small circular spot or a line pattern.

It is yet another embodiment of the present invention to provide a coagulative laser to prevent the sclera tissue bleeding when a diamond knife is used for the incision of the sclera.

It is yet another embodiment of the present invention to use a metal mask on the corneal surface to generate a small slit when the laser is scanning over the mask. In this embodiment, the exact laser spot size and its propagating stability are not critical.

It is yet another embodiment of the present invention to provide an integration system in which the sclera expansion leads to the increase of the accommodation of the ciliary muscle for the treatment of presbyopia and the prevention of open angle glaucoma.

Further preferred embodiments of the present invention will become apparent from the description of the invention which follows.

DETAILED DESCRIPTION OF THE INVENTION AND THE PREFERRED EMBODIMENTS

Figure 1:
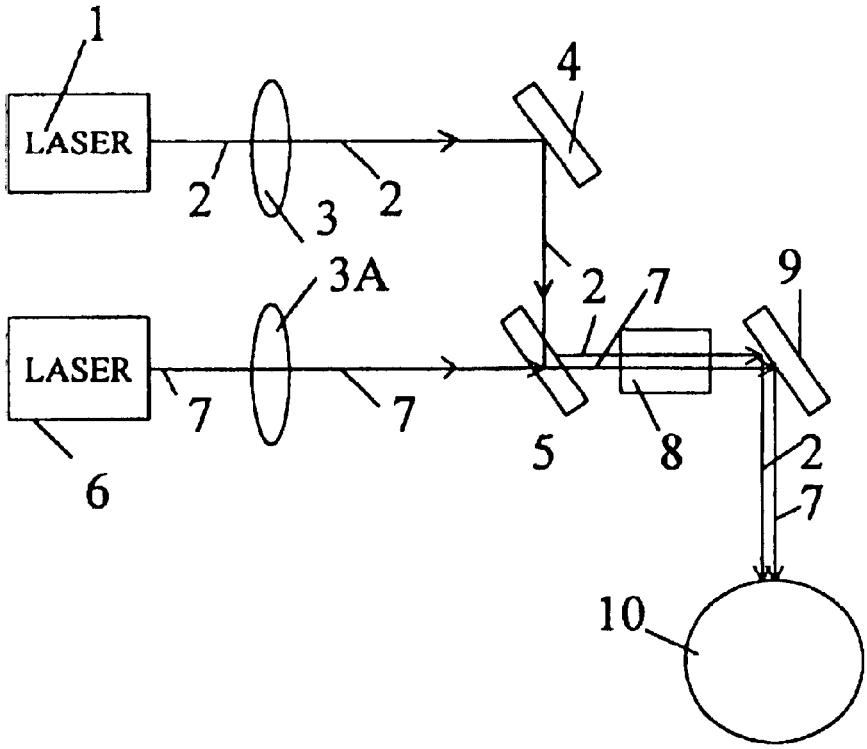
FIG. 1 is a block diagram of an integrated laser system consisting of two lasers of different wavelengths coupled to the cornea by mirrors and a scanning device.

FIG. 1 of the drawings is a schematic of a laser system having an ablative laser 1 producing a laser beam 2 of a predetermined wavelength and focused by a lens 3 onto a reflecting mirror 4 which is coupled to another reflecting mirror 5. The system also consists of a coagulation laser 6 having a laser beam 7 of a predetermined wavelength focused by a lens 3A through a mirror 5. The ablation laser 1 beam 2 and the coagulation laser 6 beam 7 are directed onto a scanner 8. The beams 2 and 7 are then reflected by a mirror 9 onto the cornea 10 of a patient's eye. The scanner 8 consists of a pair of motorized coated mirrors with a 45 degree highly reflecting both the ablative laser beam 2 and the coagulative laser beam 7. The mirror 4 and mirror 9 are highly reflective to the wavelength of the beams 2 and 7. Mirror 5 is coated such that it is highly reflective of laser beam 2 but highly transparent to laser beam 7. The focusing lens 3 has a focal length of about 10–100 cm such that the spot size of the ablative laser beam 2 is about 0.1–0.8 mm on the corneal surface. The focusing lens 3A also has a focal length about 10–100 cm such that the spot size of the coagulative laser beam 7 is about 0.2–2.0 mm on the corneal surface. In FIG. 1, both the ablative and the coagulative lasers beams 2 and 7 are scanned by the scanner 8 over the corneal sclera area of the eye 10 to generate predetermined patterns, as shown in FIG. 4. In FIG. 1, the said coagulative laser 6 is used to prevent the potential bleeding during the ablation process of the sclera tissue. Typically, the coagulative laser 6 beam 7 has a spot size larger then the ablative laser 1 beam 2 and has an average power in the range of 20–3000 mW, depending upon the size of the focused beam. To achieve an effective coagulation, the temperature increase of the sclera tissue produced by the coagulative laser beam 7 should be in the range of 40–70 degree Centigrade. The preferred embodiment of the laser 1 and 6 includes a pulsed ablative laser with a pulse width less than 200 nanoseconds such as a Er:YAG laser; Er:YSGG laser; an optical parametric oscillation (OPO) at 2.6–3.2 microns; a gas laser with a wavelength of 2.6–3.2 microns; an excimer laser of ArF at 193 nm; a XeCl laser at 308 nm; a frequency-shifted solid state laser at 0.15–3.2 microns; a CO laser at about 6.0 microns and a carbon dioxide laser at 10.6 microns. The long pulse coagulative lasers have a pulse longer than 200 nanoseconds of a green laser; or an argon laser; or a Ho:YAG at 2.1 microns; or a Er:glass at 1.54 microns; or an Er:YAG; or an Er:YSGG; or a diode laser at 0.8–2.1 microns, or any other gas lasers at 0.8–10.6 microns. To achieve the ablation of the sclera tissue at the preferred laser spot size of 0.1–0.8 mm requires an ablative laser energy per pulse of about 0.1–5.0 mJ depending on the pulse duration. On the other hand, the coagulative laser should have an, average power of about 30 mW for a small spot and about to 3 W for a larger spot.

Figure 2:
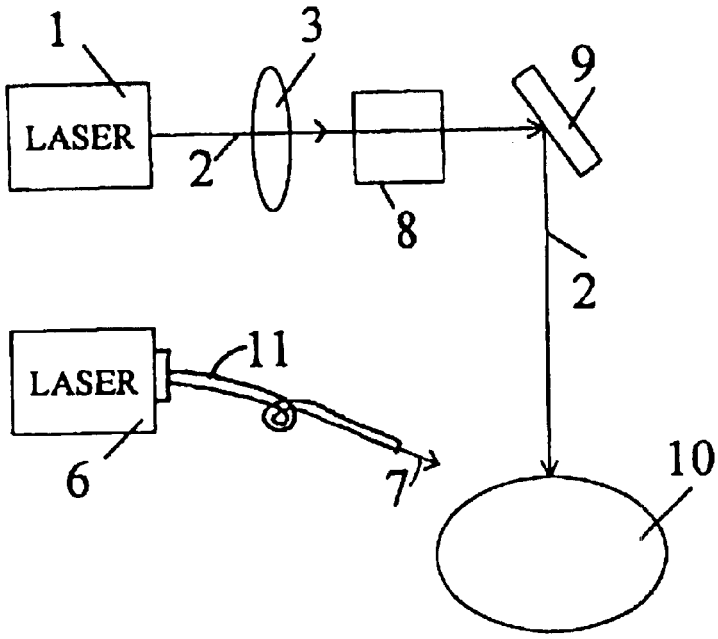
FIG. 2 is a block diagram of a laser system where the coagulative laser is fiber-coupled and manually delivered to the cornea.

Referring to FIG. 2, an alternative schematic for the coagulative laser 6 is coupled to a fiber 11 for delivery of the beam to the cornea, where a line pattern may be performed by manually scanning the beam over the cornea. Alternatively, a fiber-coupled coagulation laser 6 may be focused by a cylinder lens to form a line spot on the cornea where a typical spot size of 0.2–2.0 mm×3.0–5.0 mm is preferred. In FIG. 2, the ablative laser 1 has the same schematic as that of FIG. 1 where the laser beam 2 is coupled to the scanner 8 and reflected by the mirror 9 onto the cornea. An alternative embodiment of the present invention is to use a cylinder lens to focus the ablative laser 1 to a line spot with a size of 0.1–0.8 mm×3.0–5.0 mm on the corneal surface to eliminate the scanner 8. Another embodiment may use an optical fiber or an articulate arm to deliver both the coagulative and ablative laser beams such that the presbyopia treatment may be conducted manually without the need of a scanner or reflecting mirrors.

Figure 3:
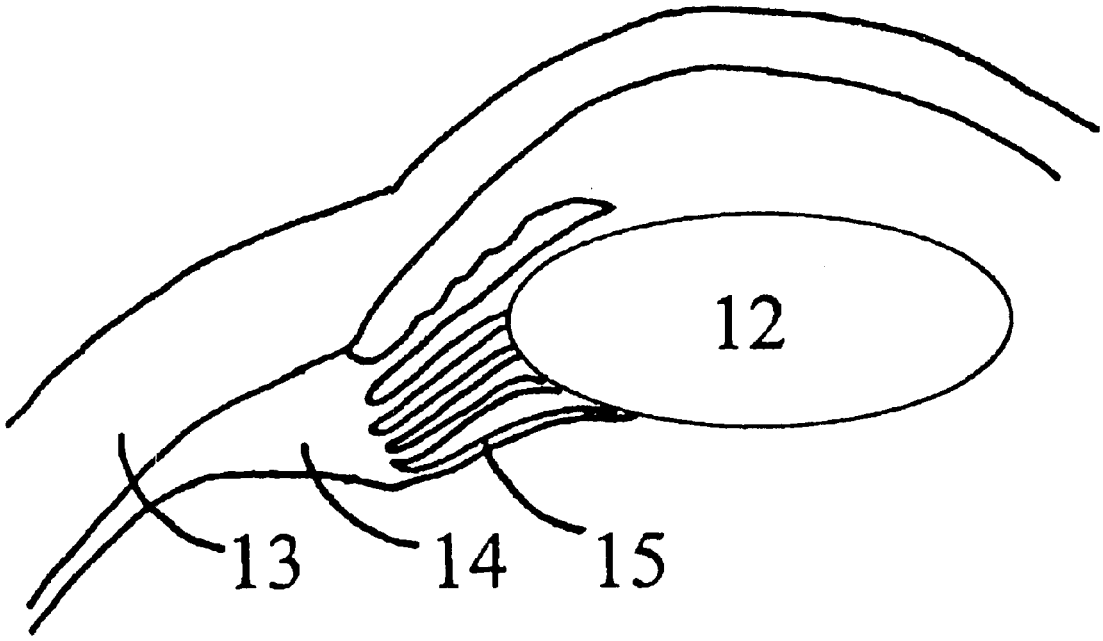
FIG. 3 is the schematic drawing of the anteroposterior section through the anterior portion of a human eye, where the sclera and ciliary muscle are shown.

FIG. 3 shows the lens of a human eye 12 connected to the sclera 13 and ciliary body 14 by zonule fibers 15. Expansion of the sclera 13 will cause the ciliary muscle to contract and the lens becomes more spherical in topography with a shorter radii of curvature for near objects. The reversed process of ciliary muscle relaxation will cause a longer radii of curvature for distant objects. Therefore, laser ablation of the sclera tissue will increase the accommodation of the ciliary body for the presbyopic patient to see both near and distance. For efficient sclera expansion, the depth of the laser ablation needs to be approximately 80%–90% of the sclera thickness which is about 500–700 microns. For safety reasons, the ablation depth should not cut through the choroid. It is therefore clinically important that the patient's sclera thickness be measured pre-operatively and the laser ablation depth controlled. A scanning laser is used to control this depth by the number of scanning lines or slots over the selected area at a given set of laser parameters. Pre-operatively, PMMA is used to calibrate the depth of tissue ablation. Alternatively, the surgeon may observe the color change of the ablated sclera tissue to determine when the ablation depth reaches the interface of the sclera and the ciliary.

FIG. 4 shows examples of ablation patterns which will cause sclera expansion and increase the accommodation of the presbyopic patient. As shown in FIG. 4A, line patterns are conducted between circles 16 and 17 which have diameters of about 8–11 mm and 12–15 mm, respectively. The width of the ablated lines are about 0.1–0.5 mm with a depth of 80%–90% of the sclera. Eight (8) lines are shown in FIG. 4A as an example but it can be more or less without departing from the spirit and scope of the invention. Enhancement may be performed by adding more ablation lines. FIG. 4B shows a ring pattern with a diameter 18 of about 12–14 mm. A two-ring pattern 19 is shown in FIG. 4C where two circles have diameters of about 10 mm and 12 mm, respectively. Another example of an ablation pattern is shown in FIG. 4D where the ablation laser is focused to a round spot 20 of about 0.1–0.5 mm in diameter and scanned over the sclera area to form an eight spot symmetric ring which has a diameter of about 12–14 mm. In all the above described ablative patterns, the coagulative laser described in FIGS. 1 and 2 simultaneously deliver these patterns such that the sclera tissue may be coagulated as the tissue is being ablated. The preferred spot sizes of the coagulative lasers are larger than that of the ablative laser so that the alignment of the coagulative laser is not critical.

Another embodiment of controlling the ablation area of the sclera area is to use a metal mask which has a plurality of slits each having an approximate dimension of 0.1–0.3 mm×3.0–5.0 mm. Both of the ablative and coagulative lasers will scan over the mask which is placed on the corneal surface to generate the desired slit pattern on the sclera. In this embodiment using a mask, the small laser spot sizes of 0.1 mm, which may be difficult to achieve, are not needed in order to generate the slit size on the cornea. Laser spot sizes of 0.2–1.0 mm will generate the desired ablation dimension on the sclera after scanning over the mask. Furthermore, the embodiment of using a mask will not require a precise stability of the laser beam path onto the corneal surface. Without using a mask, both the exact laser beam spot size and its stability in propagating would be essential.

Figure 4A:
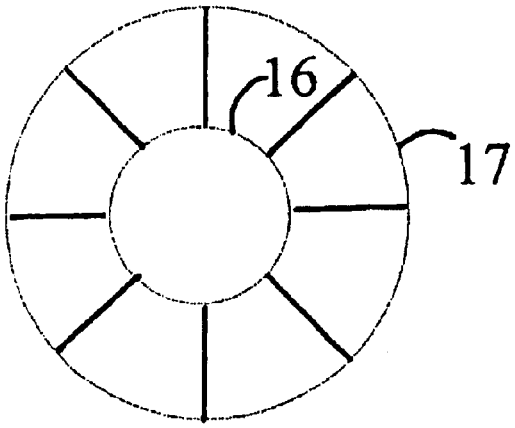
FIGS. 4A–4D are diagrams of the possible ablation patterns which will achieve a presbyopia-reversal.
Figure 4B:
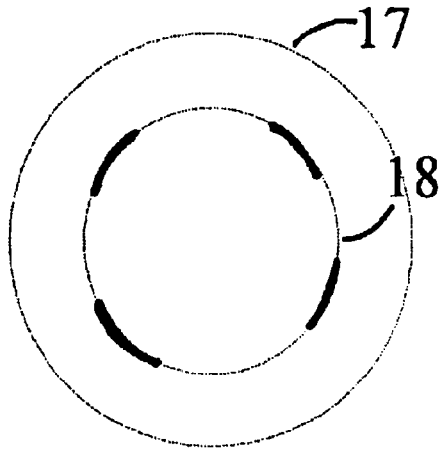
Figure 4C:
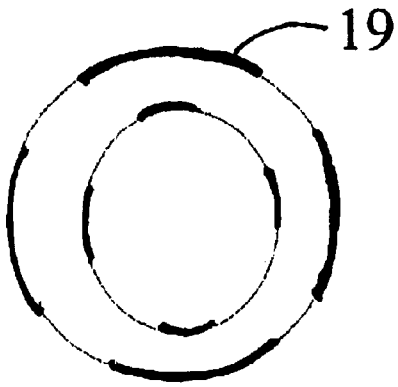
Figure 4D:
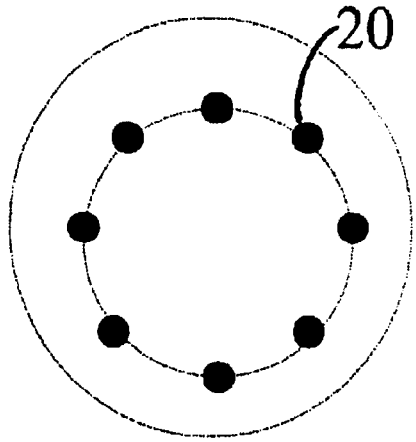

Another embodiment of sclera expansion of the present invention is to use diamond knife for the incision of the sclera tissue in the patterns described in FIGS. 4A, 4B and 4C where the coagulation laser is simultaneously applied onto the cut tissue to prevent bleeding. The incision depth should be about 80% to 90% of the sclera thickness in order to achieve the effects of sclera expansion. Accordingly, the pre-operative measurement of the sclera thickness is essential for the knife incision procedure and surgeon's skill is more important than that of using an ablative laser, in which the ablation depth of the sclera tissue is well controlled by the numbers of scanning lines in a given pattern. We are able to calibrate the ablation rate of various lasers on the sclera tissue by comparing the clinical data and that of the selected materials including a PMMA plastic sheet.

The invention having now been fully described, it should be understood that it may be embodied in other specific forms or variations without departing from the spirit or essential characteristics of the present invention. Accordingly, the embodiments described herein are to be considered to be illustrative and not restrictive.

I claim:

1. A laser beam ophthalmological surgery method for treating [presbyopic] *presbyopia* in a patient's eye by ablating the sclera comprising the steps of:

selecting a pulsed ablation laser having a pulsed output beam of predetermined wavelength;

selecting a beam spot controller mechanism for reducing and focusing said selected ablative laser's output beam onto a predetermined spot size on the surface of the [cornea] *eye*;

selecting a scanning mechanism for scanning said ablative laser output beam;

coupling said ablative laser beam to a scanning device for scanning said ablative laser over a predetermined area of the [corneal] sclera; and controlling said scanning mechanism to deliver said ablative laser beam in a predetermined pattern in said predetermined area onto the surface of the [cornea] *eye* to photoablate the sclera tissue outside the limbus *to a depth of 80–90% of the thickness of the scleral tissue*, whereby a presbyopic patient's vision is corrected by expansion of the sclera.

2. A laser beam ophthalmological surgery method for treating [presbyopic] *presbyopia* in a patient's eye by ablating the sclera in accordance with claim 1 in which the step of selecting a pulsed ablation laser includes selecting a pulsed ablative laser having a predetermined wavelength between 0.15–0.32 microns.

3. A laser beam ophthalmological surgery method for treating [presbyopic] *presbyopia* in a patient's eye by ablating the sclera in accordance with claim 1 in which the step of selecting a pulsed ablation laser includes selecting a pulsed ablative laser having a wavelength between 2.6 and 3.2 microns.

4. A laser beam ophthalmological surgery method for treating [presbyopic] *presbyopia* in a patient's eye by ablating the sclera in accordance with claim 1 in which the step of selecting a pulsed ablation laser includes selecting a solid state laser.

5. A laser beam ophthalmological surgery method for treating [presbyopic] *presbyopia* in a patient's eye by ablating the sclera in accordance with claim 1 in which the step of selecting a pulsed ablation laser includes selecting a pulsed gas laser having a pulse duration shorter than 200 nanoseconds.

6. A laser beam ophthalmological surgery method for treating [presbyopic] *presbyopia* in a patient's eye by ablating the sclera in accordance with claim 1 in which [said] the step of selecting a beam spot controller includes selecting a pulsed ablative laser having a focusing lens with focal length of between 10 and 100 cm selected to obtain a predetermined laser beam spot size having a diameter of between 0.1 and 0.8 mm on the [corneal] *eye* surface.

7. A laser beam ophthalmological surgery method for treating [presbyopic] *presbyopia* in a patient's eye by ablating the sclera in accordance with claim 1 in which the step of selecting a beam spot controller includes selecting *a* beam spot controller having a focusing lens with cylinder focal length of between 10 and 100 cm to obtain a laser beam spot having a line size of about 0.1–0.8 mm×3–5 mm on the [corneal] *eye* surface.

8. A laser beam ophthalmological surgery method for treating [presbyopic] *presbyopia* in a patient's eye by ablating the sclera in accordance with claim 1 in which the step of selecting a scanning mechanism includes selecting a scanning mechanism having a pair of reflecting mirrors mounted to a galvanometer scanning mechanism for controlling said laser output beam into a predetermined pattern.

9. A laser beam ophthalmological surgery method for treating [presbyopic] *presbyopia* in a patient's eye by an ablating laser beam in accordance with claim 1 in which said ablative laser is delivered to the surface of the [cornea] *eye* by an optical fiber.

10. A laser beam ophthalmological surgery method for treating [presbyopic] *presbyopia* in a patient's eye by ablating the sclera in accordance with claim 1 in which the step of selecting a scanning mechanism includes selecting a hand-held optical fiber coupled to the ablation laser for scanning said laser output beam into a predetermined pattern.

11. A laser beam ophthalmological surgery method for treating [presbyopic] *presbyopia* in a patient's eye by ablating the sclera in accordance with claim 1 in which the predetermined pattern is generated by the steps of:

selecting a metal mask having at least one slit therein; and positioning the selected mask over the [cornea] *eye* surface for scanning the ablation laser thereover for controlling the ablation slit pattern on the sclera tissue outside the limbus.

12. A laser beam ophthalmological surgery method for treating [presbyopic] *presbyopia* in a patient's eye by ablating the sclera in accordance with claim 1 in which said predetermined pattern includes at least 3 radial lines around the area of the cornea outside the limbus.

13. A laser beam ophthalmological surgery method for treating [presbyopic] *presbyopia* in a patient's eye by ablating the sclera in accordance with claim 1 in which said predetermined pattern includes a ring pattern around the area of the cornea outside the limbus.

*14. A method of improving accommodation and/or treating presbyopia, comprising:*

*cutting at least three spaced apart, substantially radial lines in the scleral tissue of a patient's eye outside the limbus to a depth of 80–90% of the thickness of the scleral tissue.*

*15. A method as in claim 14 wherein the lines are non-intersecting.*

*16. A method as in claim 14 wherein the step of cutting is performed using a pulsed laser.*

*17. A method as in claim 16 wherein the laser has a spot size of 0.1 mm to 0.8 mm.*

*18. A method as in claim 14 wherein the step of cutting is performed using a laser having a wavelength of approximately 2.6–3.2 microns.*

*19. A method as in claim 14 wherein the step of cutting is performed using a laser having a wavelength of about 308 nanometers.*

*20. A method as in claim 14 wherein the step of cutting is performed using a laser having a wavelength of about 193 nanometers.*

*21. A method as in claim 14 wherein the step of cutting is performed using a laser having an average power of about 30 mW to 3 W.*

*22. A method as in claim 14 wherein the step of cutting includes cutting 8 lines in the sclera.*

*23. A method as in claim 14 wherein the step of cutting includes using an optical fiber tip to deliver the laser beam to the sclera.*

* * * * *

UNITED STATES PATENT AND TRADEMARK OFFICE

CERTIFICATE OF CORRECTION

PATENT NO. : RE40,002 E
APPLICATION NO. : 10/626486
DATED : January 15, 2008
INVENTOR(S) : Jui-Teng Lin It is certified that error appears in the above-identified patent and that said Letters Patent is hereby corrected as shown below:

In Column 1, Line 9, please insert the following:

--Notice: More than one reissue application has been filed for the reissue of U.S. Patent No. 6,263,879 B1. The reissue applications include U.S. Patent Application No. 10/626,486, filed July 24, 2003 (the present, now issued, application) and U.S. Patent Application No. 12/013,950, filed January 14, 2008, which is a continuation reissue application of the present, now issued, application.--

Signed and Sealed this
Twenty-sixth Day of February, 2013

Teresa Stanek Rea
*Acting Director of the United States Patent and Trademark Office*